US00RE43984E

(19) United States
(12) Reissued Patent
Hamied et al.

(10) Patent Number: US RE43,984 E
(45) Date of Reissued Patent: Feb. 5, 2013

(54) PROCESS FOR PREPARING ISOMERS OF SALBUTAMOL

(75) Inventors: Yusuf Khwaja Hamied, Bombay (IN); Rajendra Narayanrao Kankan, Mumbai (IN); Dharmaraj Ramachandra Rao, Maharashtra (IN)

(73) Assignee: Cipla Limited (IN)

(21) Appl. No.: 12/402,752

(22) Filed: Mar. 12, 2009

Related U.S. Patent Documents

Reissue of:
(64) Patent No.: 6,995,286
Issued: Feb. 7, 2006
Appl. No.: 10/450,155
PCT Filed: Dec. 10, 2001
PCT No.: PCT/GB01/05444
§ 371 (c)(1),
(2), (4) Date: Sep. 15, 2003
PCT Pub. No.: WO02/48090
PCT Pub. Date: Jun. 20, 2002

U.S. Applications:
(62) Division of application No. 12/026,790, filed on Feb. 6, 2008.

(30) Foreign Application Priority Data

Dec. 11, 2000 (GB) ..... 0030171

(51) Int. Cl.
*C07C 229/00* (2006.01)
*C07B 57/00* (2006.01)
*C07C 59/255* (2006.01)
*C07C 213/00* (2006.01)

(52) U.S. Cl. ..... 560/42; 562/585; 564/304; 564/365

(58) Field of Classification Search ..... 560/42; 562/585; 564/304, 365
See application file for complete search history.

(56) References Cited

U.S. PATENT DOCUMENTS

| | | | |
|---|---|---|---|
| 3,644,353 | A | 2/1972 | Lunts et al. |
| 5,399,765 | A | 3/1995 | Gao et al. |
| 5,545,745 | A | 8/1996 | Gao et al. |
| 6,995,286 | B2 | 2/2006 | Hamied et al. |

FOREIGN PATENT DOCUMENTS

| | | |
|---|---|---|
| CN | 1273966 | * 11/2000 |
| JP | 02085247 | 3/1990 |
| WO | 9532178 | 11/1995 |
| WO | WO 95/32178 | 11/1995 |
| WO | 9942460 | 8/1999 |
| WO | WO 99/42460 | 8/1999 |

OTHER PUBLICATIONS

Ferrayoli et al, Resolution of racemic albuterol via diastereomeric salts formation with Di-p-toluoyl-D-tartaric acid, 2000, Enantiomer, 5(3-4),p. 289-291.*
Aldrich , Catalog Hanbdbook of Fine Chemicals, 1998-1999, p. 1543.*
Berge, S.M. et al., "Pharmaceutical Salts," *J. Pharma. Sci,* vol. 66, No. 1, pp. 1-17 (1977).
Chemical Abstracts, vol. 135, No. 7, Abstract No. 92436d, p. 775, col. 2, XP002189988 (Aug. 13, 2001).
Patent Abstracts of Japan, vol. 14, No. 280 (Jun. 18, 1990).

* cited by examiner

*Primary Examiner* — Taylor Victor Oh
(74) *Attorney, Agent, or Firm* — Merchant & Gould P.C.

(57) ABSTRACT

[A process for making optically] *Optically* pure (R) and (S) salbutamol [comprises obtaining the (R) or (S) isomer of either salbutamol or a salbutamol precursor in substantially optically pure form] *is obtained* by resolving a racemic or optically impure mixture of enantiomers of salbutamol or of [said] *a salbutamol* precursor with either (L) or (D) tartaric acid, and where necessary converting said [isomer of said] precursor into either (R) or (S) salbutamol respectively; then optionally converting said optically pure (R) and/or (S) salbutamol into a pharmaceutically acceptable salt.

11 Claims, No Drawings

PROCESS FOR PREPARING ISOMERS OF SALBUTAMOL

Matter enclosed in heavy brackets [ ] appears in the original patent but forms no part of this reissue specification; matter printed in italics indicates the additions made by reissue.

This application is *a divisional of reissue application Ser. No. 12/026,790, filed Feb. 6, 2008, which is a reissue of U.S. patent application Ser. No. 10/450,155, filed Sep. 15, 2003, now U.S. Pat. No. 6,995,286, which is* a §371 Application of International Application No. PCT/GB01/05444, filed on Dec. 10, 2001, [claiming the] *which claims* priority of Great Britain Application No. 0030171.3, filed Dec. 11, 2000[, the]. *The* entire disclosures of [which] *the priority applications listed above* are incorporated herein by reference in their entireties.

This invention relates to an improved method of making optically pure (R) and (S) salbutamol, also known as (R) and (S) albuterol. The chemical name for salbutamol is α-[[(1,1-dimethyl-ethyl)amino]methyl]-4-hydroxy-1,3-benzene-dimethanol.

For certain medical conditions such as asthma, the (R) isomer of salbutamol (which is laevorotatory, denoted (−) or (l) is known to be very much more potent therapeutically than the dextrorotatory (S) isomer. *The R isomer of salbutamol is also known as levalbuterol.* One method of preparing the (R) and (S) isomers of salbutamol in optically pure form is disclosed in U.S. Pat. No. 5,545,745. In this method, either of two precursor compounds for salbutamol is resolved using a substituted tartaric acid derivative. Specifically the resolving compound used in U.S. Pat. No. 5,545,745 is chosen from (−)-di-toluoyl-L-tartaric acid, (+)-di-toluoyl-D-tartaric acid, (−)-di-benzoyl-L-tartaric acid and (+)-di-benzoyl-D-tartaric acid. Another reference (Hartley et al, Journal of Medicinal Chemistry, 1971, Vol 14, No 9, pp 895-896) describes much the same thing as U.S. Pat. No. 5,545,745: the resolution is performed with either (+) or (−) di-para-toluoyl tartaric acid. A more recent publication (WO 99/42460) describes the resolution of a new ketal derivative of salbutamol (specifically 2-(N-t-butylamino)-1-(+2,2-dimethyl-1,2-benzodioxin-6-yl) ethanol). The resolution is again performed with a chiral tartaric acid derivative, such as (+) or (−) di-para-toluoyl tartaric acid or (+) or (−) di-O-benzoyl tartaric acid. Enantiomers of salbutamol can be produced if desired, via a complicated, multi-stage process involving resolution of the ketal derivative. The disadvantage of the process described in WO 99/42460 is that the enantiomeric excess of the salts obtained is low (based on the values given in the Examples). This requires additional crystallizations, thus lowering the overall yields. Further, two additional synthetic steps of ketalization and hydrolysis further reduces the economic viability of the process.

Whilst the process of U.S. Pat. No. 5,545,745 is an improvement over previous methods of resolution, it nevertheless has certain disadvantages. The substituted tartaric acid derivatives employed are expensive (and not readily available) and so need to be specially prepared or bought, which adds to the overall time and cost of the process. These resolving compounds are generally not recovered from the process and this further contributes to the costs.

We have now found a way of substantially overcoming these problems. In particular, we have found an economical and efficient method of resolving salbutamol into its optically pure (R) and (S) isomers, which method does not require the use of expensive substituted tartaric acid derivatives.

According to the present invention, there is provided a process for making optically pure (R) and/or (S) salbutamol or pharmaceutically acceptable salts thereof, which process comprises obtaining the [(E)] *(R)* or (S) isomer of either salbutamol or a salbutamol precursor in substantially optically pure form by resolving a racemic or optically impure mixture of enantiomers of salbutamol or of said precursor with either (L) or (D) tartaric acid, and where necessary converting said isomer of said precursor into either (R) or (S) salbutamol respectively; then optionally converting said optically pure (R) and/or (S) salbutamol into a pharmaceutically acceptable salt.

Unlike the substituted tartaric acid derivatives used in U.S. Pat. No. 5,545,745, (L) and (D) tartaric acid are readily available and inexpensive. They can be recovered and re-used in the process if desired, although even when they are not re-used the process is much more economical than that described in U.S. Pat. No. 5,545,745.

An advantage of the present method is its general applicability to different intermediates of salbutamol. It also enables chirally pure product to be obtained in a good yield.

In a highly preferred aspect of the invention, the compound 4-benzyl albuterol (i) (α-[[(1,1- dimethylethyl) amino]methyl]-4-(phenylmethoxy)-1,3-benzenedimethanol) is used as the salbutamol precursor. A racemic or optically impure mixture of the compound is resolved to give the (R) and (S) isomers before conversion to the desired isomer of salbutamol takes place. 4-benzyl albuterol is readily available commercially, for example from Cipla Limited.

The precursor 4-benzyl albuterol is typically prepared, for example, from the ester intermediate methyl-5-[2-[(1,1-dimethylethyl)amino]-1-hydroxyethyl]-2-(phenylmethoxy)-benzoate (II).

(II)

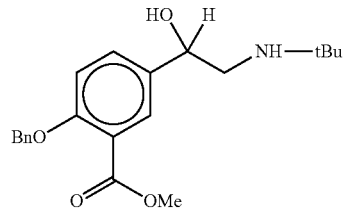

Bn = benzyl
tBu = tertiary butyl

This compound (II) can also, if desired, serve as the "salbutamol precursor" which is itself resolved into its (R) and (S) isomers.

We have found that the present method of resolution can be used satisfactorily to resolve racemic salbutamol (or an optically impure mixture of enantiomers of salbutamol) itself.

Thus, in a further aspect, the invention provides a process for making optically pure (R) and/or (S) salbutamol or pharmaceutically acceptable salts thereof, which process comprises resolving racemic salbutamol, or an optically impure mixture of enantiomers of salbutamol, with either (L) or (D) tartaric acid, and optionally converting said optically pure (R) and/or (S) salbutamol into a pharmaceutically acceptable salt thereof.

The present invention thus provides several ways of producing (R) and/or (S) salbutamol: by resolution at the final stage, for example on racemic salbutamol, or by resolution at an intermediate stage—for example, by resolution of the alcohol intermediate 4-benzyl albuterol or by resolution of the ester intermediate (II) methyl-5-[2-[(1,1-dimethylethyl) amino]-1-hydroxyethyl]-2-(phenylmethoxy)-benzoate.

We prefer to operate the process using (L) tartaric acid, since this results in the more active isomer (R) salbutamol. However, the invention encompasses the production of (S) salbutamol, in which case (D) tartaric acid is used in the resolution step.

By the term "optically pure", we mean an enantiomeric excess (e.e.) (which is a measure well known in the art) of about 95% or more. The term "optically impure" refers to mixtures of enantiomers where the e.e. value is below about 95%, but where the mixture is not exactly racemic. We have found that the resolution step with (L) or (D) tartaric acid is very efficient, generally giving an e.e. value of 99% or more for the chosen isomer.

Operation of the process using our preferred precursor 4-benzyl albuterol is preferably carried out according to the following Scheme A below:

Scheme A

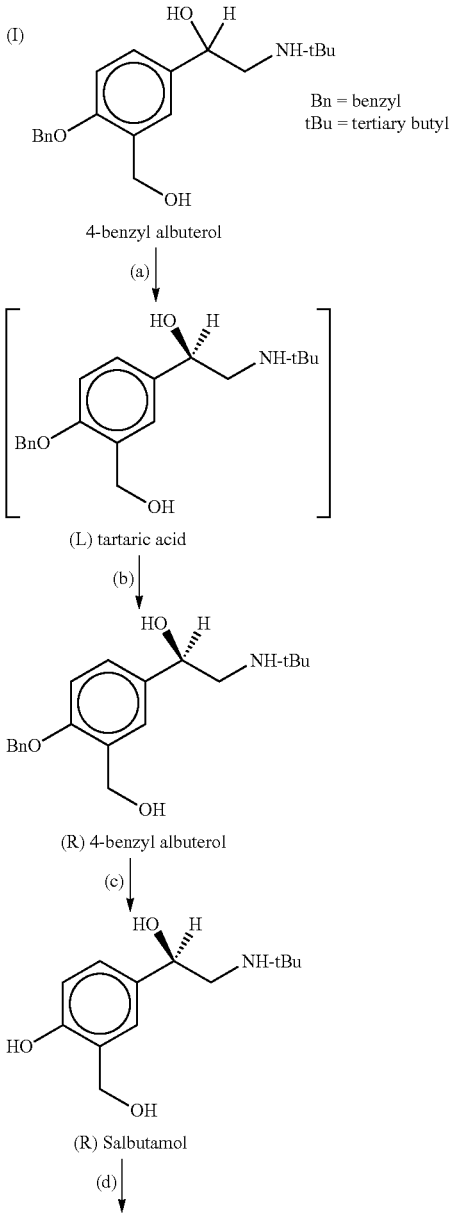

-continued

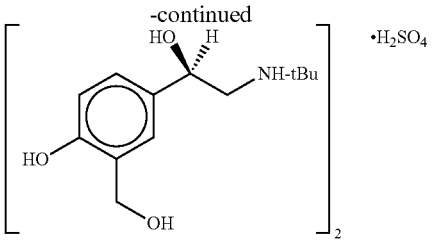

(R) salbutamol sulphate

In step (a) a suspension of racemic 4-benzyl albuterol is mixed with a solution of either (L) or (D) tartaric acid (as desired) in an organic solvent. We prefer to use a solvent such as methanol, ethanol, isopropanol, acetone or ethyl acetate or a mixture of two or more thereof. The mixture is then chilled to give crystals of the (L) or (D) tartrate salt of 4-benzyl albuterol, which are then separated and purified. The yield of the chosen tartrate salt is generally above 30%, with an e.e. value of around 99%.

In step (b), the optically pure isomer of either (R) or (S) 4-benzyl albuterol is obtained from a solution (typically aqueous) of the corresponding tartrate salt. We prefer to liberate the free base from the tartrate salt by the gradual addition of alkali to the solution of the salt, for example by using sodium hydroxide or sodium carbonate. Other bases that can be used include potassium hydroxide, potassium carbonate, aqueous ammonia and sodium or potassium bicarbonate. Prolonged stirring of the alkali/salt mixture is usually necessary to precipitate the free base completely from the solution. The yield of the (R) or (S) isomer of 4-benzyl albuterol is generally 40% or more based on the quantity of racemic starting material. The e.e. value remains high, typically at 99% or more.

In step (c), (R) or (S) 4-benzyl albuterol free base is debenzylated in order to give (R) or (S) salbutamol. This is preferably carried out by suspending the isomer of 4-benzyl albuterol in an organic solvent such as ethanol, adding a palladium on carbon catalyst and hydrogenating the suspension under pressure in a hydrogenator. The resulting optically pure isomer of salbutamol is then filtered off. If desired, a pharmaceutically acceptable salt of the free base can be obtained by the addition of an acid (for example, dilute sulphuric or hydrochloric acid) in the usual way (see step (d)).

Alternatively, the resolving-step can if desired be carried out earlier in the process, for example, by resolving the ester intermediate (II). (L) or (D) tartaric acid may be used for the resolution, although preferably (L) tartaric acid is employed so as to give the (R) form of the ester. This preferred route is shown in Scheme B below.

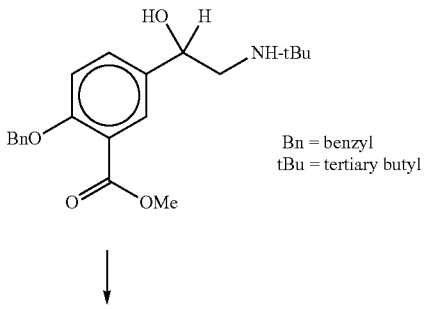

-continued

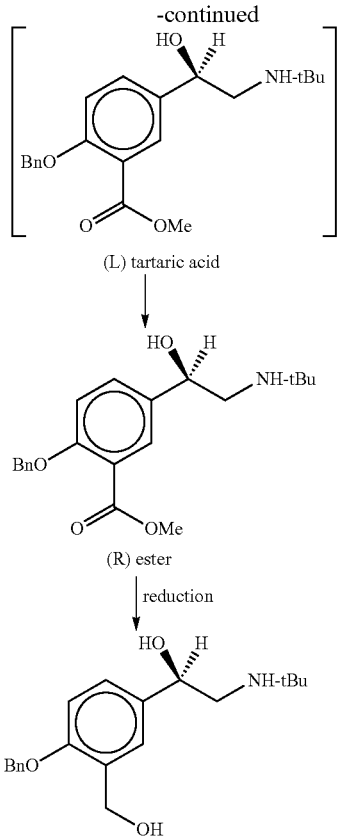

The reduction of the (R) isomer of the ester to (R) 4-benzyl albuterol can, for example, be carried out using lithium aluminium hydride, although any suitable reducing agent can be used. The resolution is typically carried out in the same way as that described for 4-benzyl albuterol.

Other salbutamol precursors which can be usefully employed in the process of the invention include derivatives of 4-benzyl albuterol in which the ring of the benzyl group is variously substituted. The benzyl group may, for example, be substituted with one or more halogen atoms (such as, chlorine, fluorine or bromine) or one or more alkoxy groups such as methoxy. Other similar substitutions which have the purpose of protecting the phenolic group of the salbutamol precursor may also be used, as will be clear to those skilled in the art.

The following examples are intended to illustrate the invention:

EXAMPLE 1

Preparation of R-4-Benzyl Albuterol-L-tartrate:

Racemic 4-benzyl albuterol (100 g, 0.30 mole) is suspended in methanol (500 ml) and heated to reflux. A solution of L-tartaric acid (50 g, 0.33 mole) in methanol (150) ml is introduced in about 15 minutes. The clear solution is then chilled to 0 to 5° C. and the crystals are filtered. The wet crystals are taken up in isopropanol (300 ml) and heated to reflux, cooled to room temperature and filtered to obtain the title compound as a white solid (65 g, 45% yield, 99% ee)

EXAMPLE 2

Preparation of R(−)-4-Benzyl Albuterol:

The product from Example 1 (65 g, 0.13 mole) is dissolved in water (650 ml) and filtered over celite to remove insolubles. The clear filtrate is cooled to 10° C. and a solution of 10% sodium hydroxide (80 ml) is slowly introduced. The sticky solid precipitated becomes free on prolonged stirring for 4 hours. The solid is filtered, washed with water and dried to obtain the title compound as a white solid (40 g, 40% yield based on amount of racemic compound, 99% e.e.).

EXAMPLE 3

Preparation of R(−) Salbutamol Sulphate:

R-4-Benzyl Albuterol (40 g, 0.12 mole) is suspended in 500 ml ethanol, 5% palladium on carbon (2 g) is added and shaken in a 1 lit. Parr Hydrogenator at 30 psi for 2 hours. The catalyst is filtered off and the clear filtrate is cooled to 15° C. under stirring. Sulphuric acid (4.9 g, 0.05 mole) is introduced dropwise and the resulting mixture is stirred for 1 hour and filtered. The solids are washed with ethanol (20 ml) and dried at 45 to 50° C. in a vacuum oven to give pure R-salbutamol sulphate (30 g, 86% yield).

EXAMPLE 4

Preparation of R(−) methyl-5-[2-[(1,1-dimethylethyl) amino]-1-hydroxyethyl]-2-(phenylmethoxy)-benzoate:

Racemic ester (100 g, 0.28 mole) is suspended in methanol (600 ml) and heated to reflux. A solution of L-tartaric acid (50 g, 0.33 mole) in methanol (150 ml) is introduced in about 30 minutes. The clear solution is then chilled to 0 to 5° C. and the crystals are filtered. The wet crystals are taken up in ethanol (400 ml) and heated to reflux, cooled to room temperature and filtered to obtain the R(−) ester-L-tartrate as a white solid. This is then dissolved in water (500 ml) and filtered over celite to remove insolubles. The clear filtrate is then cooled to 0 to 5° C. and an aqueous ammonia solution is introduced so as to obtain a pH of 8.5 to 9. The mass is then stirred for 3 hours and the solids filtered, washed with water and dried to obtain the title compound (38 g; 38% yield based on racemic compound, 99% e.e.).

EXAMPLE 5

Preparation of R(−)-4-benzyl Albuterol Using R(−)ester of Example 4:

R(−)-ester (35.8 g, 0.1 mole) is suspended in dry tetrahydrofuran (250 ml) and cooled to 0 to 5° C. Lithium aluminium hydride (4 g; 0.33 mole) is introduced slowly and the reaction mass is further stirred for 3 hours. A 15% sodium sulphate (20 ml) is then introduced and the precipitate is then filtered off. The clear filtrate is then concentrated, taken up in ethyl acetate (100 ml), cooled to 5° C. and filtered to obtain the title compound (30 g; 91%; 99% e.e.).

EXAMPLE 6

Preparation of (S)4-benzyl Albuterol-(D)-tartrate

Racemic 4-benzyl albuterol (100 g, 0.30 mole) is suspended in methanol (500 ml) and heated to reflux. A solution of (D-)tartaric acid in methanol (150 ml) is introduced in about 15 minutes. The clear solution is then chilled to 0 to 5° C. and the crystals filtered. The wet crystals are taken up in isopropanol (300 ml) and heated to reflux, cooled to room temperature and filtered to obtain the title compound as a white solid (65 g; 45%; 99% e.e.).

EXAMPLE 7

Preparation of (S)-4-benzyl Albuterol:

The product from Example 6 (65 g; 0.13 mol) is dissolved in water (650 ml) and filtered over celite to remove insolubles. The clear filtrate is cooled to 10° C. and a solution of 10% sodium hydroxide (80 ml) is slowly introduced. The solids thus precipitated are filtered, washed with water and dried to obtain the title compound as a white solid (40 g; 40% based on racemic compound, 99% c.c.).

EXAMPLE 8

Preparation of (S)-salbutamol Sulphate:

(S)-4- benzyl albuterol (40 g; 0.12 mole) is suspended in 500 ml ethanol, 5% palladium on carbon (2 g) is added and shaken in a 1 litre Parr hydrogenator at 30 psi for 2 hours. The catalyst is then filtered off and the clear filtrate is cooled to 15° C. Sulphuric acid (4.9 g; 0.05 mole) is added dropwise and the resultant mixture is stirred for 1 hour and filtered. The solids are washed with ethanol (20 ml) and dried to give pure (S)-salbutamol sulphate (30 g; 86%).

EXAMPLE 9

Salbutamol (100 g; 0.41 mole) is dissolved in a 1:1 mixture of ethyl acetate and methanol (500 ml) at about 70° C. To this solution is added L(+)tartaric acid (66 g; 0.44 mole) under stirring. The contents are maintained at 70° C. for 2 hours. On cooling, the tatrate salt crystallises. This is filtered and recrystallised from ethanol to give 52 g of the pure R (−) salbutamol tartrate. The salt is then suspended in methanol (200 ml) and a solution of sodium methoxide (15 g; 0.27 mole) in methanol is introduced. The precipitated solids are filtered off and the filtrate is cooled to 10° C. Sulphuric acid is added slowly to obtain a pH of the reaction mass between 4 to 4.5. The solids are filtered and dried to obtain R(−)salbutamol sulphate (30 g).

What is claimed is:

[1. A process for making optically pure (R) salbutamol or pharmaceutically acceptable salts thereof having a value of 95% enantiomeric excess or more, which process comprises obtaining the (R) isomer of either salbutamol or a salbutamol precursor, wherein the salbutamol precursor is 4-benzyl albuterol or methyl-5-[2-[(1,1-dimethylethyl)amino]-1-hydroxyethyl]-2-(phenylmethoxy)-benzoate in optically pure form by:

a) dissolving a mixture of salbutamol, 4-benzyl albuterol or methyl-5-[2-[(1,1-dimethylethyl)amino]-1-hydroxyethyl]-2-(phenylmethoxy)-benzoate enantiomers and a molar excess (with respect to said salbutamol or said precursors) of (L) tartaric acid in a solvent;

b) allowing the solution to cool to crystalize a salt of one enantiomer;

c) separating the salt from the solution;

d) liberating the enantiomer from the salt;

e) when the enantiomer is 4-benzyl albuterol or methyl-5-[2-[(1,1-dimethylethyl)amino]-1-hydroxyethyl]-2-(phenylmethoxy)-benzoate, reducing the enantiomer; and f) except when salbutamol is used in step a), debenzylating the enantiomer and recoVering the (R) enantiomer of salbuamol; then optionally converting said optically pure (R) salbutamol into a pharmeucedically acceptable salt.]

[2. A process according to claim 1, wherein the mole equivalent amount of tartaric acid is greater than or equal to 1.07.]

[3. A process according to claim 1, wherein the mole equivalent amount of tartaric acid is greater than or equal to 1.1.]

[4. A process according to claim 1, wherein the mole equivalent amount of tartaric acid is at least 1.18.]

[5. A process according to claim 1, wherein the salbutamol precursor is 4-benzyl albuterol.]

[6. A process according to claim 1, wherein the resolution is carried out on racemic salbutamol or on an optically impure mixture of enantiomers of salbutamol.]

[7. A process according to claim 1, wherein the optical purity has a value of 99% enantiomeric excess or more.]

[8. A process according to claim 1, further comprising converting said isomer of said precursor into either (R) salbutamol respectively; then optionally converting said optically pure (R) salbutamol into a pharmaceutically acceptable salt.]

*9. Pure and isolated Levalbuterol L-tartrate having an enantiomeric excess of at least 95%.*

*10. Levalbuterol L-tartrate as claimed in claim 9, which is in crystalline form.*

*11. An optically-pure 4-benzyl albuterol salt of tartaric acid, selected from the group consisting of optically pure (R)-4-benzyl albuterol-(L)-tartrate salt and optically pure (S)-4-benzyl-albuterol-(D)-tartrate salt.*

*12. The optically-pure 4-benzyl albuterol salt of tartaric acid of claim 11, where the optically pure (R)-4-benzyl albuterol-(L)-tartrate salt is present in an enantiomeric excess of greater than about 99%.*

*13. The optically-pure 4-benzyl albuterol salt of tartaric acid of claim 11, where the optically pure (S)-4-benzyl albuterol-(D)-tartrate salt is present in an enantiomeric excess of greater than about 99%.*

*14. An optically-pure methyl-5-[2-[(1,1-dimethylethyl) amino]-1-hydroxyethyl]-2-(phenylmethoxy)-benzoate salt of tartaric acid, selected from the group consisting of optically pure (R)-methyl-5-[2-[(1,1-dimethylethyl)amino]-1-hydroxyethyl]-2-(phenylmethoxy)-benzoate(L)-tartrate salt and optically pure (S)-methyl-5-[2-[(1,1-dimethylethyl) amino]-1-hydroxyethyl]-2-(phenylmethoxy)-benzoate-(D)-tartrate salt.*

*15. The optically-pure methyl-5-[2-[(1,1-dimethylethyl) amino]-1-hydroxyethyl]-2-(phenylmethoxy)-benzoate salt of tartaric acid of claim 14, where the optically pure (R)-methyl-5-[2-[(1,1-dimethylethyl)amino]-1-hydroxyethyl]-2-(phenylmethoxy)-benzoate-(L)-tartrate salt is present in an enantiomeric excess of greater than about 99%.*

*16. The optically-pure methyl-5-[2-[(1,1-dimethylethyl) amino]-1-hydroxyethyl]-2-(phenylmethoxy)-benzoate salt of tartaric acid of claim 14, where the optically pure (S)-methyl-5-[2-[(1,1-dimethylethyl)amino]-1-hydroxyethyl]-2-(phenylmethoxy)-benzoate-(D)-tartrate salt is present in an enantiomeric excess of greater than about 99%.*

*17. A pure and isolated salbutamol salt of tartaric acid having an enantiomeric excess of at least 95% selected from the group consisting of (R)-salbutamol-(L)-tartrate salt and (S)-salbutamol-(D)-tartrate salt.*

*18. The pure and isolated salbutamol salt of tartaric acid of claim 17, where the (R)-salbutamol-(L)-tartrate salt is present in an enantiomeric excess of greater than about 99%.*

*19. The pure and isolated salbutamol salt of tartaric acid of claim 17, where the (S)-salbutamol-(D)-tartrate salt is present in an enantiomeric excess of greater than about 99%.*

* * * * *